United States Patent [19]

Fisher

[11] 4,211,234

[45] Jul. 8, 1980

[54] ENDOTRACHEAL TUBE INTRODUCER

[76] Inventor: Joseph Fisher, 67 Tanjoe Ct., Willowdale, Ontario, Canada

[21] Appl. No.: 936,536

[22] Filed: Aug. 24, 1978

[51] Int. Cl.² ............................................ A61M 25/00
[52] U.S. Cl. ................................ 128/200.26; 128/343
[58] Field of Search .............................. 128/348–351, 128/341, 343, 345, 4–8, 208, 242–244

[56] References Cited

U.S. PATENT DOCUMENTS

| 2,442,573 | 6/1948 | Stafford | 128/242 |
|---|---|---|---|
| 3,044,461 | 7/1962 | Murdock | 128/343 X |
| 3,169,529 | 2/1965 | Koenig | 128/351 |
| 3,968,800 | 7/1976 | Vilasi | 128/351 |
| 4,068,658 | 1/1978 | Berman | 128/351 |
| 4,090,518 | 5/1978 | Elam | 128/351 X |
| 4,141,364 | 2/1979 | Schultze | 128/351 |

*Primary Examiner*—Dalton L. Truluck
*Attorney, Agent, or Firm*—Ivor M. Hughes

[57] ABSTRACT

An endotracheal tube introducer comprising a rigid hollow mouth piece of greater diameter than the endotracheal tube being inserted thereinto, and an elongated member secured to and extending longitudinally away from the mouth piece, the elongated member comprising at least one guide rib extending longitudinally along the length of the elongated member away from the mouth piece and relatively thin pliable film pleated longitudinally and secured to the at least one guide rib and forming with the at least one guide rib, when the film is unpleated, an enclosed tubular structure for guiding the endotracheal tube into the trachea.

20 Claims, 10 Drawing Figures

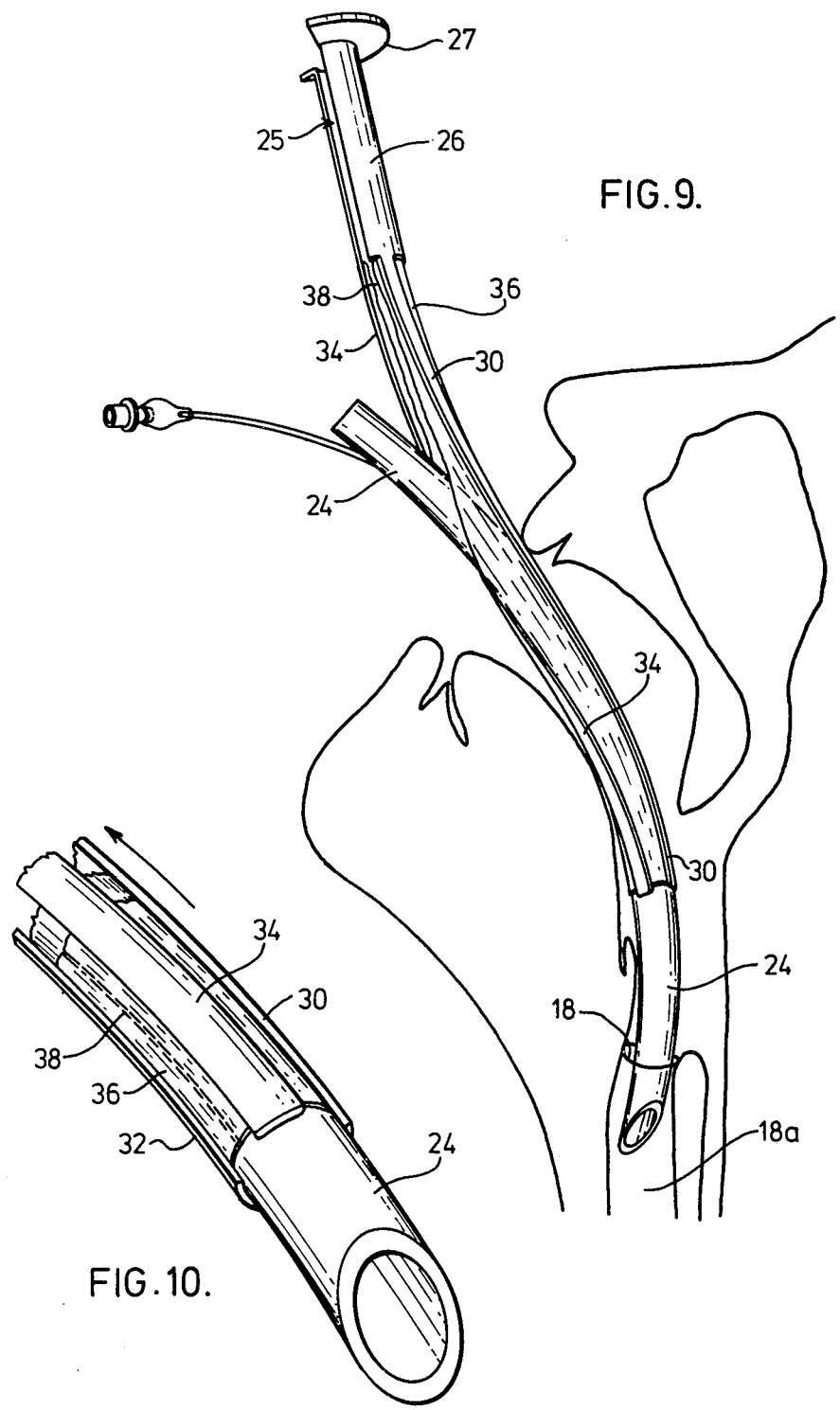

4,211,234

ENDOTRACHEAL TUBE INTRODUCER

FIELD OF INVENTION

This invention relates to an endotracheal tube introducer.

BACKGROUND OF THE INVENTION

The inability of any patient to breath is a life or death situation. Oxygen must immediately be forced into the patient's lungs otherwise the patient will die.

With the patient lying prone, a laryngoscope is positioned with the blade in the patient's mouth lying against the tongue and extending to the epiglottis and both the tongue and epiglottis are pulled forward and the tongue depressed to expose the vocal cords. Attempts are then made to introduce an endotracheal tube past the vocal cords into the trachea, either with or without the use of an endotracheal tube introducer. In many instances, the vocal cords and tissues of the pharynx are "taut" and passage therebetween of any structure of considerable cross-sectional area relative to the space, of the pharynx or between the vocal cords, is very difficult. The use of the endotracheal tube introducers previously proposed, and over which introducer the endotracheal tube rides, is not effective in all situations. Particularly, they have not provided the reliability and effectiveness in situations where the vocal cords have "seized" or an anatomic narrowing of the pharynx passage occurred which passage would not "open" for the passage of the endotracheal tube riding over the endotracheal tube introducer. In that case, the cross-sectional area of the endotracheal tube approaches that of the pharynx, restricting the pharynx for accurate placement of the endotracheal tube, and precluding manoeuverability in the pharynx for proper placement. In one particular case, the vocal cords could not be forced, despite repeated attempts at intubation, and the patient died.

Furthermore, because the endotracheal tube rides over the guide, the effect of the attempted intubation on the vocal cords and surrounding tissue (anatomic fold and oedema) is as if the endotracheal tube were inserted without the guide—the tissue and cords are traumatized.

It is therefore an object of this invention to provide an endotracheal tube introducer which is highly reliable and effective and which causes minimal trauma to the vocal cords and surrounding tissue.

SUMMARY OF THE INVENTION

To provide reliable intubation, this invention contemplates an endotracheal tube introducer which easily penetrates between the vocal cords into the trachea and which expands as an endotracheal tube is advanced therethrough, effectively separating the vocal cords and permitting passage of the endotracheal tube into the trachea. The endotracheal tube introducer may then be removed.

Therefore, in accordance with one aspect of the invention, an endotracheal tube introducer is provided comprising a hollow mouth piece preferably being rigid and of greater diameter than the endotracheal tube, preferably having a longitudinally extending slot, extending along the length of the mouth piece, the slot being preferably about the diameter of the endotracheal tube, and a relatively thin elongated member, secured to, and extending longitudinally away from, the mouth piece, the elongated member comprising at least one guide rib extending longitudinally along the length of the elongated member away from the mouth piece and a relatively thin pliable material pleated longitudinally, secured to the at least one guide rib and forming, with the at least one guide rib when unfolded, an enclosed tubular structure for guiding the endotracheal tube therethrough into the trachea.

According to another aspect of the invention, the pliable material may be provided with a separation line along its length in aligned relation to the slot, when the slot is provided, in the mouth piece to assist in the removal of the endotracheal tube introducer following successful intubation.

According to another aspect of the invention, the at least one guide rib comprises three ribs spaced from one another, preferaly at an angle of 120° to one another, and the pliable material is a length of tubing preferably pleated longitudinally and to which material each of the guide ribs is secured.

According to another aspect of the invention, a radially outwardly extending annular flange may be secured to the outer wall of the mouth piece remote the end to which the elongated member is secured. Where the slot is provided along the length of the mouth piece, the annular flange extends only partly around the mouth piece, being interrupted at least adjacent the slot. The mouth piece may be made from high density polyethylene, polypropylene or other suitable material and the thin pliable material may be polyethylene or Cellophane (t.m.) or other suitable material and the mouth piece and elongated members may be separately manufactured and secured to one another at the time of use as for example, by a coupling, zippered structure or interlocking hooks.

In use, under direct laryngoscopy, the vocal cords are penetrated by the end of the elongated member remote the mouth piece with preferably the endotracheal tube supported in the mouth piece, and the endotracheal tube advanced from the mouth piece into the elongated member. As the tube is advanced into the interior of the member, the thin pliable material ahead of the tube is sequentially unfolded or expanded pushing the at least one guide outwardly. When the endotracheal tube in the elongated member is near the vocal cords, the expanding or unfolding of the material and the at least one guide rib spreads the vocal cords and soft tissues to permit penetration therethrough by the endotracheal tube with minimal trauma to the vocal cords and surrounding tissue. The introducer may then be removed over the positioned endotracheal tube. Where the slot and separation line are provided, the introducer is pulled upwardly with the tube angled to protrude from the slot and overlie the separation line. Then the introducer is pulled upwardly so that the tube successively separates the material along the separation line as the introducer is removed.

The invention will now be illustrated having regard to the following drawings of the preferred embodiment and detailed description of the preferred embodiment.

BRIEF DESCRIPTION OF THE DRAWINGS

FIG. 9 illustrates the removal of the endotracheal tube introducer according to the preferred embodiment of the invention;

FIG. 10 is a close-up part of the endotracheal tube introducer and endotracheal tube shown in FIG. 9;

DETAILED DESCRIPTION OF THE PREFERRED EMBODIMENTS OF THE INVENTION

Figure 1:
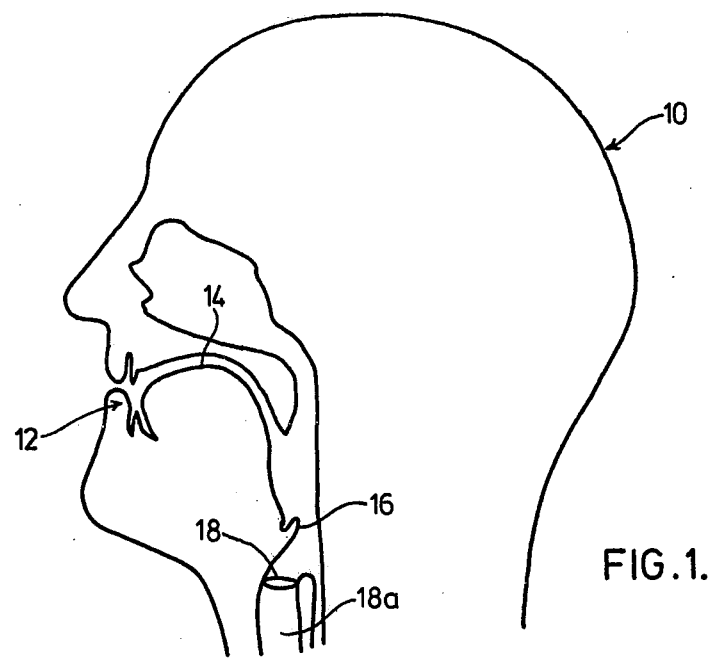
FIG. 1 is a schematic side view drawing of the human head showing the mouth, tongue, epiglottis, trachea and oesophagus.
Figure 2:
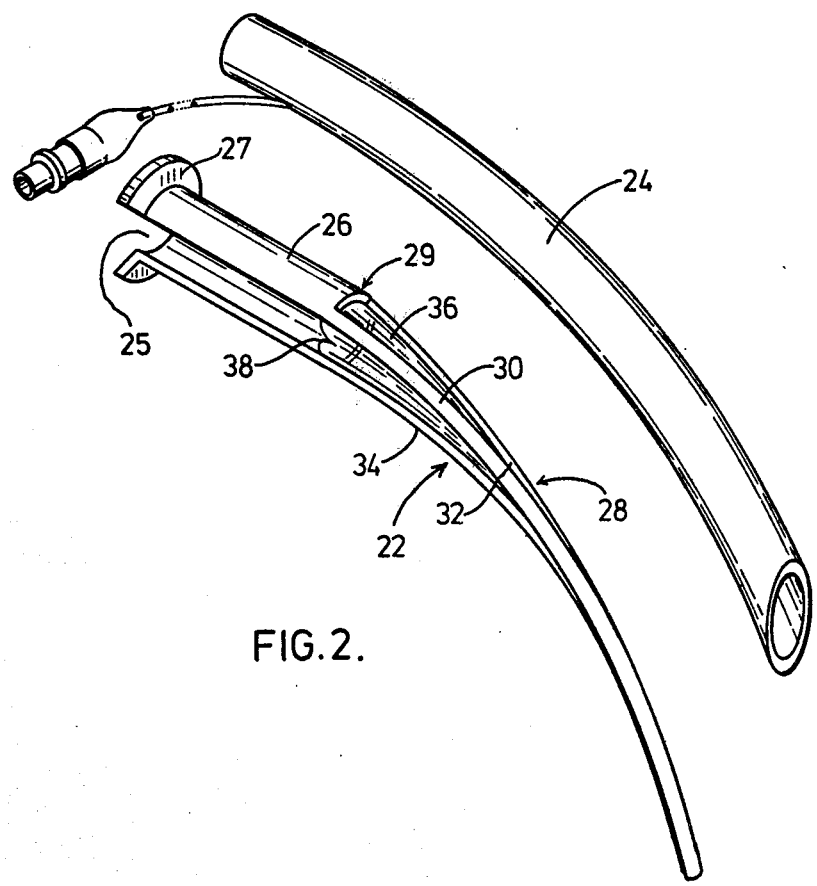
FIG. 2 is a perspective view of an endotracheal tube and endotracheal tube introducer according to the preferred embodiment of the invention.
Figure 3:
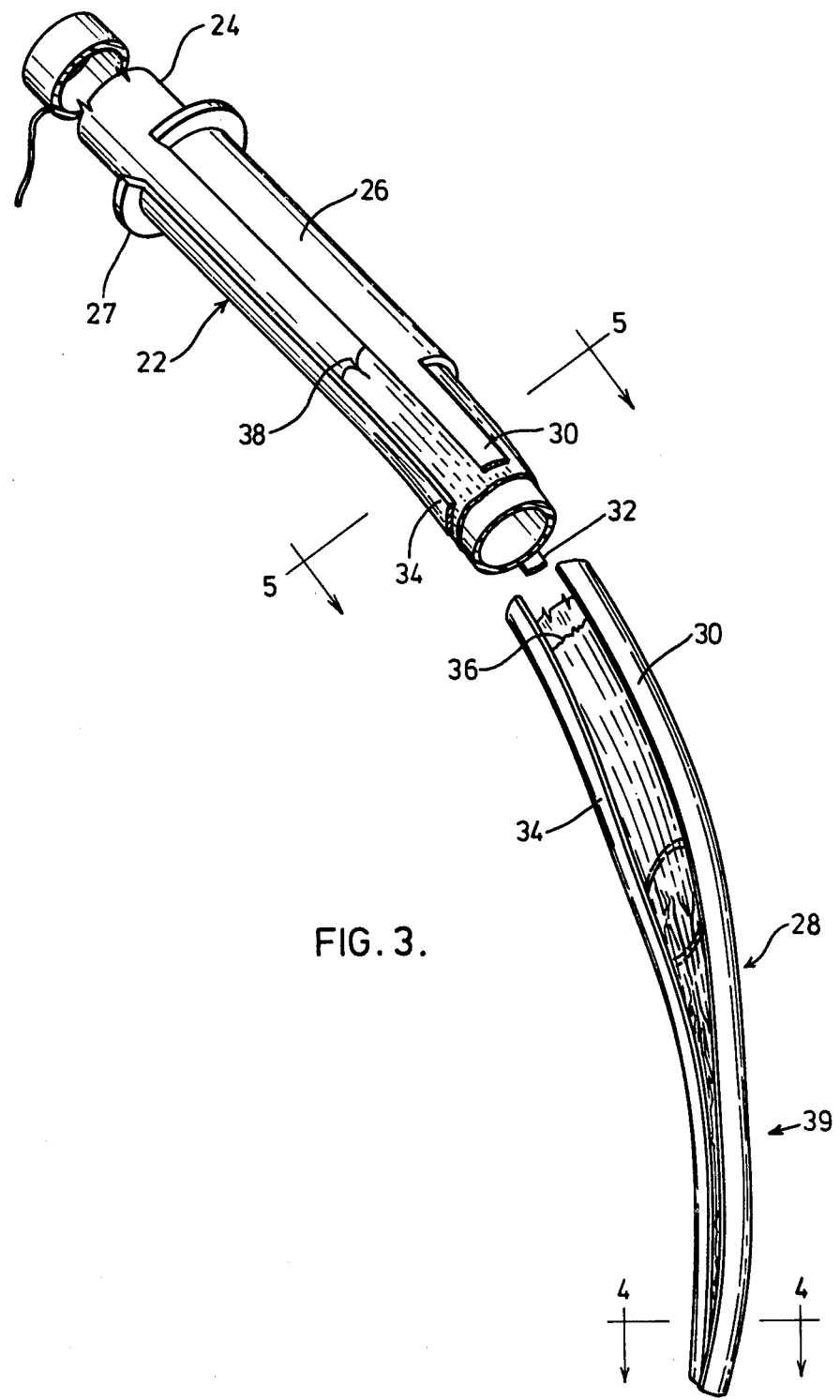
FIG. 3 is a perspective view of the endotracheal tube partially inserted into the endotracheal tube introducer according to the preferred embodiment of the invention.
Figure 7:
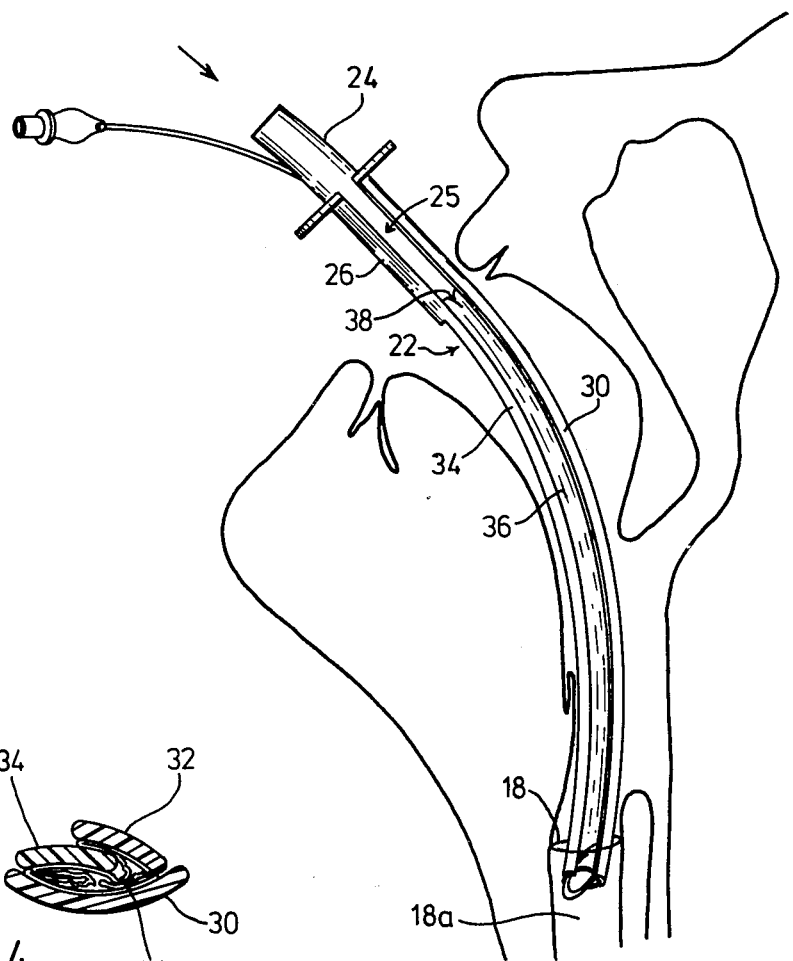
FIG. 6 and FIG. 7 (found with FIGS. 3 and 4) illustrate the use of the endotracheal tube and endotracheal tube introducer according to the preferred embodiment of the invention.
Figure 4:
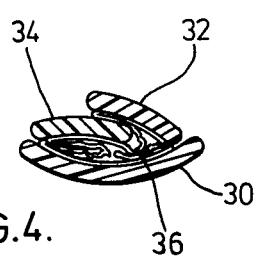
FIG. 4 is a section taken along the line 4—4 of FIG. 3.
Figure 5:
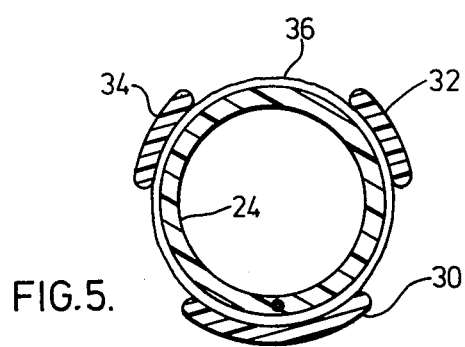
FIG. 5 is a section taken along the line 5—5 in FIG. 3.
Figure 8:
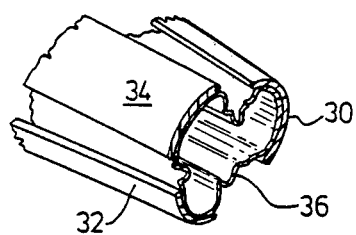
FIG. 8, (found with FIG. 6) is a partially unfolded perspective view of the end of the endotracheal tube introducer according to a preferred embodiment of the invention.
Figure 6:
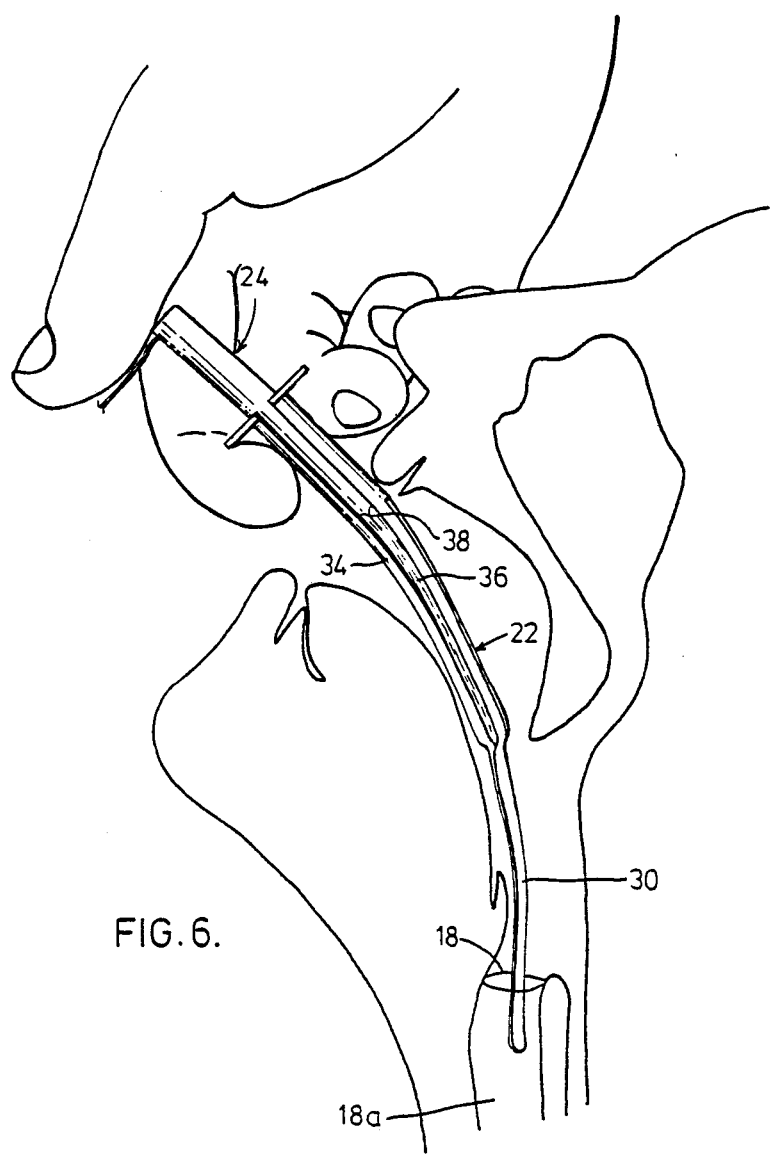

With reference to FIG. 1, there is shown diagrammatically and in cross-section a head of patient 10, illustrating his/her mouth 12, tongue 14, epiglottis 16, trachea 18a, larynx 18, vocal cords (not shown), and oesophagus 20. As is evident, to be able to see the larynx 18 (and vocal cords) through the mouth of the patient 12 into which an endotracheal tube is to be introduced, the patient must be lying prone with his/her back and his/her tongue pulled forward and depressed by a laryngoscope (not shown);

According to the preferred embodiment of the invention, an endotracheal tube introducer 22 for introducing an endotracheal tube passed the vocal cords into the trachea is provided—its construction best shown in FIGS. 2 and 3, and method of use best shown in FIGS. 6, 7, and 8; With reference to FIGS. 2 and 3, there is shown endotracheal tube introducer 22 in conjunction with endotracheal tube 24. Since the construction of an endotracheal tube 24 is well known in the art, a description of its structure will not be included herein. The endotracheal tube introducer 22 includes cylindrical mouth piece 26 made of rigid plastics material, longitudinally extending slot 25 along its length, flange 27 extending around the upper end of the mouth piece, interrupted adjacent the slot, and an elongated member 28 comprising three guide ribs 30, 32 and 34, rib 30 being wider than either of ribs 32 and 34, the ribs being spaced at a 120° angle to one another, and extending away from the end 29 of mouth piece 26 longitudinally of the elongated member, ribs 32 and 34, separated by a distance to permit endotracheal tube 24 to pass therebetween. Secured to these ribs is a length of tubular film material 36 pleated down its length (best shown in cross-section in FIG. 4) so that along the elongated member's length, ribs 30 32 and 34 are proximate one another and form a very restricted lumen in which the longitudinally pleated film 36 is gathered. Aligned with slot 25 and extending along the length of tubular film 36 is tear line 38 for the purposes hereinafter discussed;

With reference to FIG. 3, the endotracheal tube 24 has been partially inserted into the mouth piece and driven lengthwise into elongated member 22 towards the other end of elongated member 28. As can be seen, as the endotracheal tube is advanced into the elongated member, the pleated tubular material has been expanded and the ribs pushed radially outwardly (seen best in FIG. 5) to accommodate the endotracheal tube. However, because the leading edge of the endotracheal tube passing down the length of the elongated member shown in FIG. 3 has not approached the section of the endotracheal tube introducer, shown in FIG. 4, the material remains in its original pleated or folded fashion with the guide ribs 30, 32 and 34 being proximate one another;

In use, the combination of the endotracheal tube 24 and endotracheal tube introducer 22 shown in FIG. 6, is inserted into the throat with the help of the laryngoscope (not shown), so that the lower end 39 of elongated member 28 is pushed past the vocal cords (not shown) into the trachea with the fingers securely holding on to the mouth piece 26 by the use of flange 27 (as shown), and rib 30 lying against the back of the larynx. The endotracheal tube is then advanced along the length of the interior of the elongated member into the throat. As it does so, it sequentially radially forces both the pleated film and the ribs 30, 32 and 34 radially outwardly. Therefore, when the endotracheal tube 24 (within introducer 22) is near the vocal cords, the guide ribs are pushed radially outwardly and gently spread the vocal cords for entry of the endotracheal tube, seen best in FIG. 7;

Once the endotracheal tube 24 has been fully pushed into the trachea, the endotracheal tube introducer is removed as shown in FIG. 10. Endotracheal tube 24 is angled relative to endotracheal tube introducer 22 to project out slot 25 and introducer 22 is withdrawn generally upwardly. As endotracheal tube introducer 22 is withdrawn upwardly as shown, endotracheal tube 24 engages tear line 38 in film 36 causing it to tear to permit removal of introducer 22 leaving the endotracheal tube in place.

As many changes could be made in the invention without departing from the scope thereof, it is intended that all matter contained herein be interpreted as illustrative of the invention and not in a limiting sense.

The embodiments of the invention in which an exclusive property or privilege is claimed are as follows:

1. An endotracheal tube introducer comprising a hollow mouth piece of greater diameter than the endotracheal tube being inserted thereinto, and an elongated member secured to and extending longitudinally away from the mouth piece, for insertion thereof past the epiglottis into the trachea, the elongated member comprising at least one guide rib extending longitudinally along the length of the elongated member away from the mouth piece and relatively thin pliable material pleated longitudinally and secured to the at least one guide rib and forming with the at least one guide rib, when the material is unfolded an enclosed tubular structure for guiding the endotracheal tube into the trachea.

2. The endotracheal tube of claim 1 wherein the mouth piece is rigid and has a slot extending longitudinally of the mouth piece of a width to permit an endotracheal tube to be pushed therethrough.

3. The endotracheal tube of claim 1, wherein the mouth piece is rigid and a flange extends radially outwardly from the mouth piece.

4. The endotracheal tube of claim 2 wherein a flange extends radially outwardly from the mouth piece being interrupted adjacent the slot.

5. The endotracheal tube introducer of claim 1 wherein the film is provided with a separation line along its length.

6. The endotracheal tube introducer of claim 2 wherein the film is provided with a separation line along its length in aligned relation to the slot in the mouth piece.

7. The endotracheal tube introducer of claim 1 wherein the at least one guide rib comprises three ribs spaced relative to one another.

8. The endotracheal tube introducer of claim 1 wherein the pliable material is a length of tubing of film pleated longitudinally and to which tubing of film the at least one guide rib is secured.

9. The endotracheal tube introducer of claim 7 wherein the mouth piece has a slot extending longitudinally of the mouth piece of a width to permit an endotracheal tube to be pushed therethrough.

10. The endotracheal tube introducer of claim 9 wherein the film is provided with a separation line along its length in aligned relation to the slot in the mouth piece.

11. The endotracheal tube introducer of claim 10 wherein the space between the guide ribs separated by the film portion in which the separation line is disposed, is of sufficient width to permit an endotracheal tube to be pushed therebetween.

12. The endotracheal tube introducer of claim 8 wherein the mouth piece has a slot extending longitudinally of the mouth piece of a width to permit an endotracheal tube to be pushed therethrough.

13. The endotracheal tube introducer of claim 12 wherein the film is provided with a tear line along its length in aligned relation to the slot in the mouth piece.

14. The endotracheal tube introducer of claim 13 wherein the space between the guide ribs separated by the film portion in which the separation line is disposed, is of sufficient width to permit an endotracheal tube to be pushed therebetween.

15. The endotracheal tube of claim 8 wherein the at least one guide rib comprises three ribs spaced relative to one another.

16. The endotracheal tube of claim 15, wherein the mouth piece has a slot extending longitudinally of the mouth piece of a width to permit an endotracheal tube to be pushed therethrough.

17. The endotracheal tube of claim 16 wherein the film is provided with a tear line along its length in aligned relation to the slot in the mouth piece.

18. The endotracheal tube of claim 17 wherein the space between the guide ribs separated by the film portion in which the tear line is disposed, is of sufficient width to permit an endotracheal tube to be pushed therebetween.

19. The endotracheal tube of claim 14 wherein a flange extends radially outwardly from the mouth piece being interrupted adjacent the slot.

20. The endotracheal tube of claim 18 wherein a flange extends radially outwardly from the mouth piece being interrupted adjacent the slot.

* * * * *